US012800562B2

(12) United States Patent
Maltese et al.

(10) Patent No.: US 12,800,562 B2
(45) Date of Patent: Nov. 17, 2026

(54) ANTHROPOMORPHIC CO2 BREATHING DEVICE

(71) Applicant: X-Biomedical, Inc., Bryn Mawr, PA (US)

(72) Inventors: Matthew R. Maltese, Wallingford, PA (US); Mario Mischewski, Marthod (FR)

(73) Assignee: X-Biomedical, Inc., Bryn Mawr, PA (US)

( * ) Notice: Subject to any disclaimer, the term of this patent is extended or adjusted under 35 U.S.C. 154(b) by 84 days.

(21) Appl. No.: 19/075,939

(22) Filed: Mar. 11, 2025

(65) Prior Publication Data

US 2025/0285561 A1 Sep. 11, 2025

Related U.S. Application Data

(60) Provisional application No. 63/563,729, filed on Mar. 11, 2024.

(51) Int. Cl.
*G01N 33/00* (2006.01)

(52) U.S. Cl.
CPC ....... *G01N 33/004* (2013.01); *G01N 33/0016* (2013.01)

(58) Field of Classification Search
CPC . G09B 23/303; G01N 33/004; G01N 33/0016
USPC .......................................... 434/262; 73/31.02
See application file for complete search history.

(56) References Cited

U.S. PATENT DOCUMENTS

2025/0153536 A1* 5/2025 Sebastian ........... B60H 1/00585

* cited by examiner

*Primary Examiner* — Robert P Bullington, Esq.
(74) *Attorney, Agent, or Firm* — Schott, P.C.

(57) ABSTRACT

A breathing simulation apparatus includes a lung enclosure in fluid communication with a positive pressure valve where the lung enclosure is sealed such that fluid flow through a trachea input creates a positive pressure inside the lung enclosure that acts against simulated lungs therein. This positive pressure, during an exhale cycle, simulates an exhale. During an inhale cycle, the positive pressure is released, and the simulated lungs fill with fluid to simulate an inhale. A carbon dioxide source adds carbon dioxide to the exhalation to simulate the conversion of breathable air into carbon dioxide in the lungs.

15 Claims, 7 Drawing Sheets

ANTHROPOMORPHIC CO2 BREATHING DEVICE

STATEMENT REGARDING GOVERNMENT SUPPORT

This invention was made with government support under Contract No. 6913G624C100014 awarded by the United States Department of Transportation. The government has certain rights in the invention.

BACKGROUND

"A 3-year-old boy died after his father thought he dropped him off at daycare on his way to work. The father went to pick his son up at daycare where he thought he was, only to find out he forgot his child in the car that morning."

"A 15-month-old girl died in Mason, Ohio when her mother realized she forget her in the car that morning when she got to work. After she got a call from her husband that their child was not at daycare when he went to pick her up, she realized what went wrong."

"A 2-year-old girl died in Arizona after finding her way to the garage while everyone else in the house was asleep. She climbed into the car and accidentally locked herself in. When her father found her, it was too late."

These tragic deaths of children are each one of many preventable tragedies caused by pediatric vehicular hyperthermia (PVH)-children locked in cars in the hot sun who eventually die from excessive heat. According to the US National Highway Traffic Safety Administration (NHTSA), 936 children have died in hot cars since 1998. The age range is between 5 days and 14 years old, and more than half of the children are under 2 years old. In 53% of cases, the child was forgotten by their caregiver, followed by the child gaining vehicle access on their own (25%) and then knowingly left in the vehicle by their caregiver (20%). Wisely, the United States Department of Transportation, National Highway Traffic Safety Administration (NHTSA) has prioritized the evaluation of sensor systems in vehicles for the ability to detect unattended children and prevent heat stroke occurrence. Some in the industry have developed sensors based upon weight, pressure, video, radar, sound, ultrasound, or a combination thereof. Recently, innovators have developed systems that detect children present in the vehicle by measuring carbon dioxide (CO2) in the vehicle cabin.

CO2 is, of course, a byproduct of mammalian respiration, and these innovators assert that a child (or adult or animal) left in a hot car would increase the level of CO2 to a detectable level; upon detection of elevated CO2 the vehicle could activate the HVAC system to cool the interior, and alert caregivers and EMS by cellular phone, and proximal bystanders by horn, lights, and audio announcement.

The NHTSA is responsible for ensuring the effectiveness of safety systems in motor vehicles sold within the United States. Through Federal Motor Vehicle Safety Standards (FMVSS), test procedures and performance limits are set and enforced. FMVSS that evaluate human-to-vehicle interactions typically involve a human surrogate that is human-like or biofidelic. For example, FMVSS 213 tests the effectiveness of child restraint systems in mitigating head, chest, and lower extremity injury in frontal crashes and uses a crash test dummy or anthropomorphic test device (ATD) to represent the human in the crash test.

Safety systems that prevent vehicular hyperthermia are no exception to the NHTSA's mandate to evaluate the effectiveness of sensors and related safety technology. That is, current crashworthiness ATDs likely effectively evaluate sensor systems that rely on weight, pressure, and shape, and a manikin that reproduces human infant motion at rest has already been developed (CPD Dummy, Messring, Gilching, Germany).

Thus, developing a CO2 Release Test Device would fill an important gap in the NHTSA's mandate and in the global safety community.

SUMMARY OF THE EMBODIMENTS

A breathing simulation apparatus includes a lung enclosure in fluid communication with a positive pressure valve where the lung enclosure is sealed such that fluid flow through a trachea input creates a positive pressure inside the lung enclosure that acts against simulated lungs therein. This positive pressure, during an exhale cycle, simulates an exhale. During an inhale cycle, the positive pressure is released, and the simulated lungs fill with fluid to simulate an inhale. A carbon dioxide source adds carbon dioxide to the exhalation to simulate the conversion of breathable air into carbon dioxide in the lungs.

DETAILED DESCRIPTION OF THE EMBODIMENTS

Figure 1A:
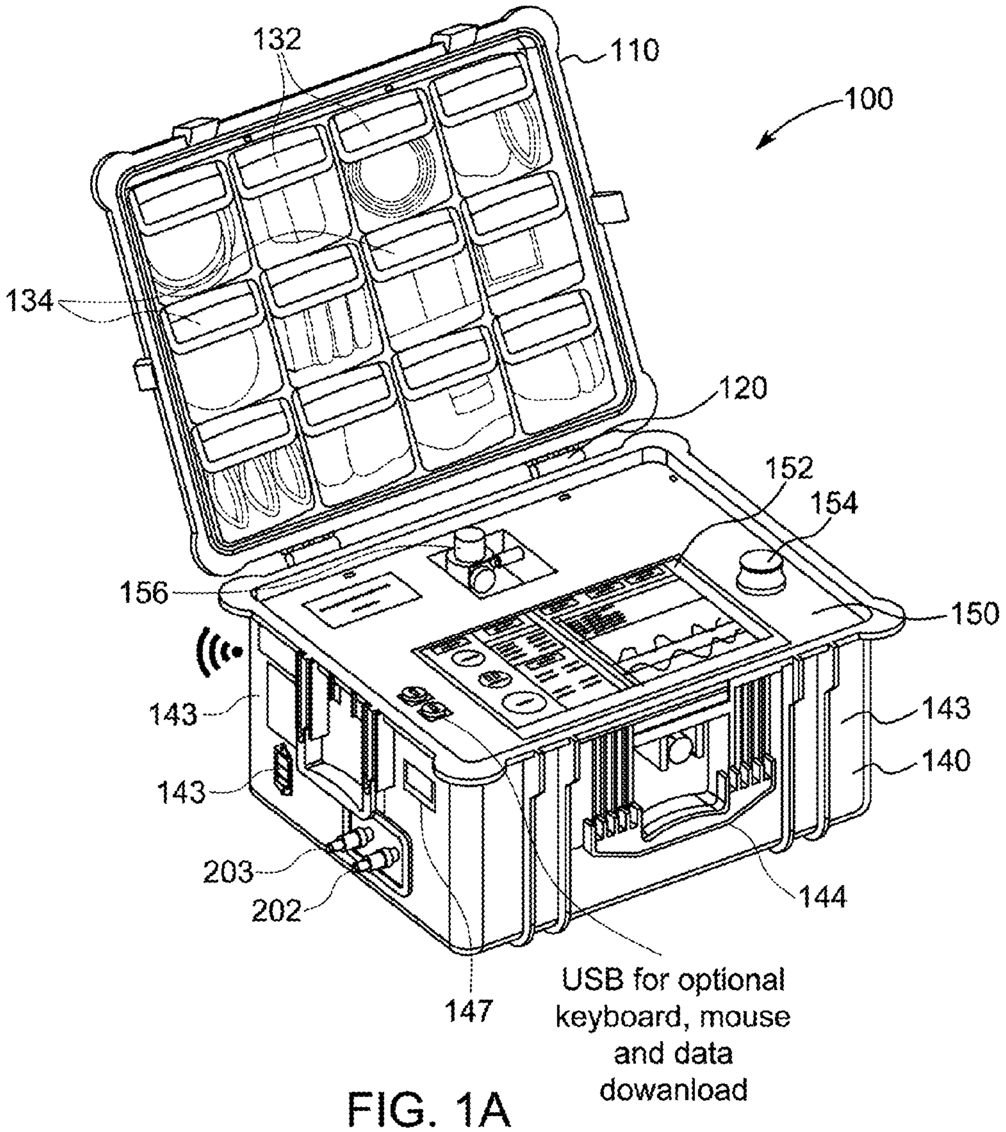
FIGS. 1A-1C show an overview of the anthropomorphic CO2 breathing device
Figure 1B:
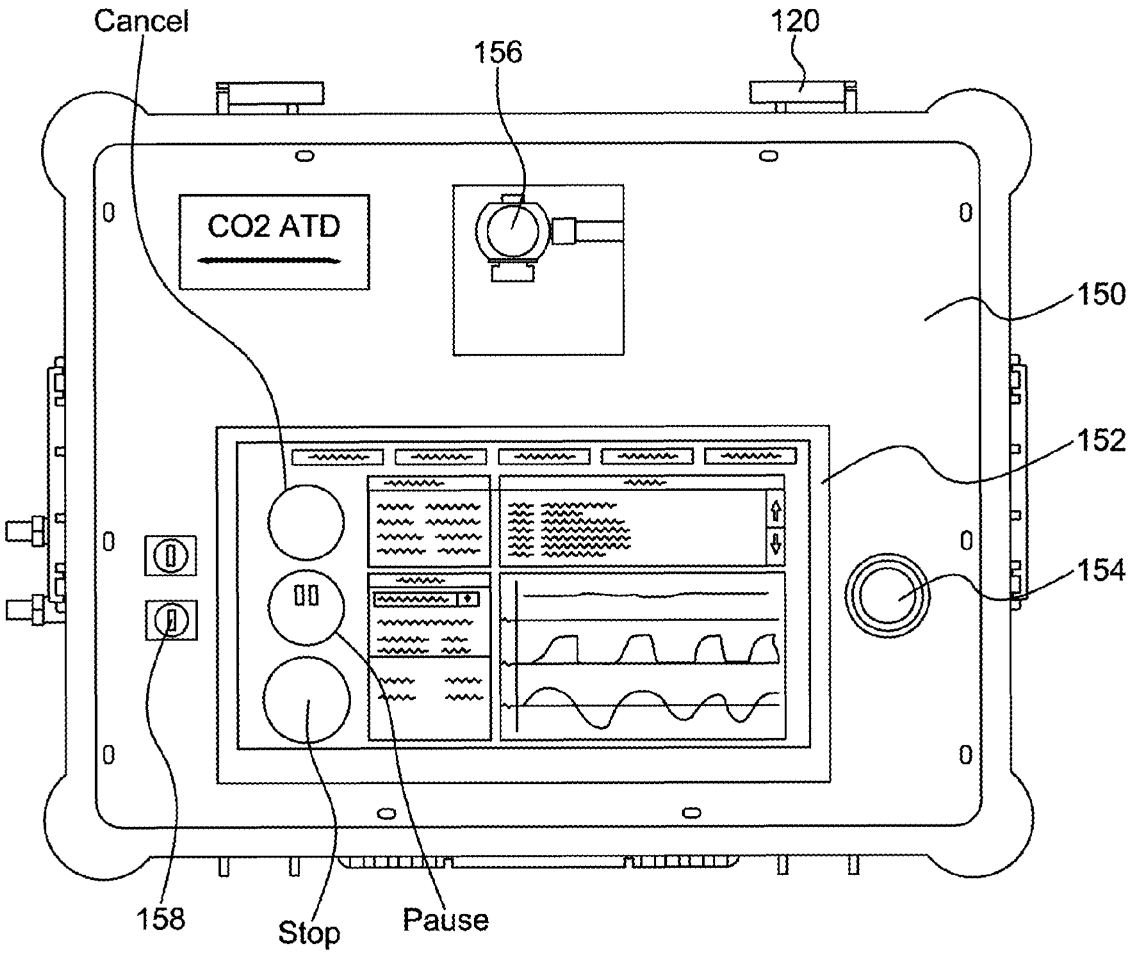
Figure 1C:
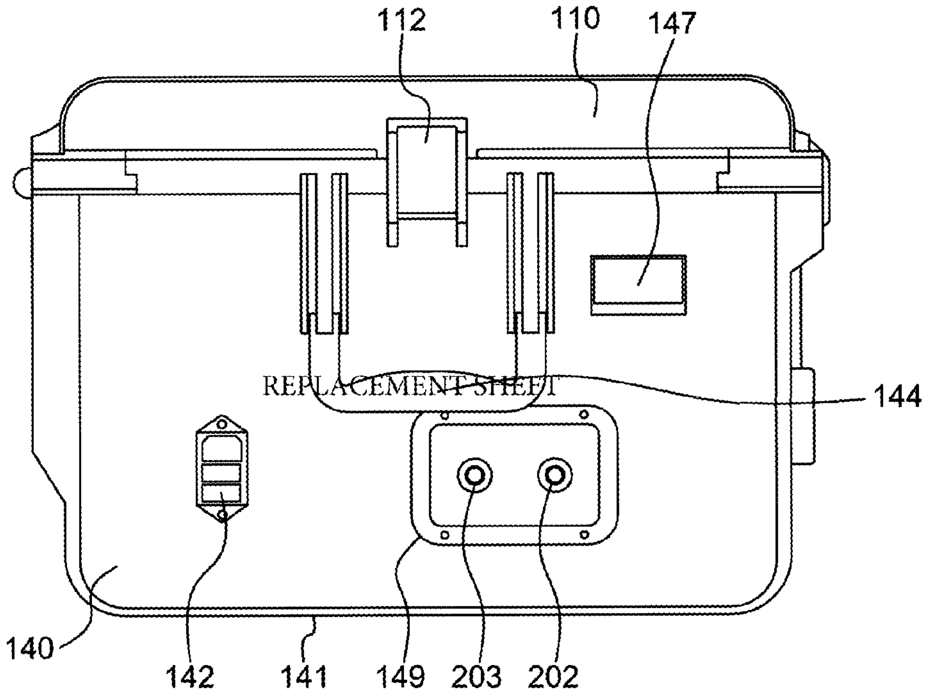

FIGS. 1A-1C show an overview of the anthropomorphic CO2 breathing device 100. FIG. 1C shows the breathing device 100 in its closed form, and FIGS. 1A and 1B in its closed form. As shown, the device measures 649×517×342 mm and fits comfortably on a standard automobile seat or rests on an infant safety car seat. It may also be placed next to or inside a human or animal mannequin.

Looking at the breathing apparatus 100, its exterior shell includes a lid 110 and main compartment 140. The lid 110 may be removable from the main compartment 140, or as shown, hinged via a hinge 120 therebetween. At least one latch 112 secures the lid 110 to the storage compartment 140. The latch 112 ensures that during breathing apparatus transport, perhaps using the handles 144, the breathing apparatus 100 remains in its closed configuration. There may be a seal between the exterior edges of the lid 110 and the main compartment 140 to ensure a clean condition inside the breathing apparatus 100.

The lid 110 may include accessories 132 within a recessed area 130, which accessories may be useful in operating the breathing apparatus 100. The accessories 132 may include tubing CO2 cartridges, and other replacement or operational parts, and the accessories 132 may be stored in resealable pockets 134 or otherwise secured in the recessed area 130.

The main compartment 140 may include an AC power connector port 142, trachea connections 202, 203, and an external status display 147 that shows certain status information about the breathing apparatus, when activated.

The trachea connections 202, 203 may extend through an insert 149 attached to an opening in a sidewall 143 of the main compartment 140. The reason for making this insert removable is that this may be an area subject to more wear or damage and thus, replacing the insert 149 is less costly than replacing the entire main compartment 140. The insert 149, as shown, is also recessed. The insert 149 may engage a cap (not shown) that protects the trachea connections 202, 203 from contamination or damage when not in use.

The main compartment 140 may engage, within a cavity defined by its sidewalls 143 and bottom 141, a decking 150. The decking 150 has a depth within the main compartment cavity such that it does not interfere with the components below it (see FIG. 2). The decking 150 may have through-holes or define decking cavities that operate and/or control the breathing apparatus 100.

For example, the decking 150 may engage a display 152 with detailed digital controls, feedback, and system status. The display 152 may be a touch sensitive screen or it may be controlled by a push and rotate control knob 154, or it may be controlled remotely or in a wired connection to another remote device. The decking 150 may include access ports 156 that allow for easy insertion and removal of CO2 canisters. The decking could also include USB or other ports 158 that allow for data download or control devices to interact with the breathing apparatus 100.

The decking 150 engages the main compartment sidewalls 143 such that the operational cavity 200 defined between the decking 150 and the bottom 141 of the main compartment 140 is protected from contamination.

Figure 2:
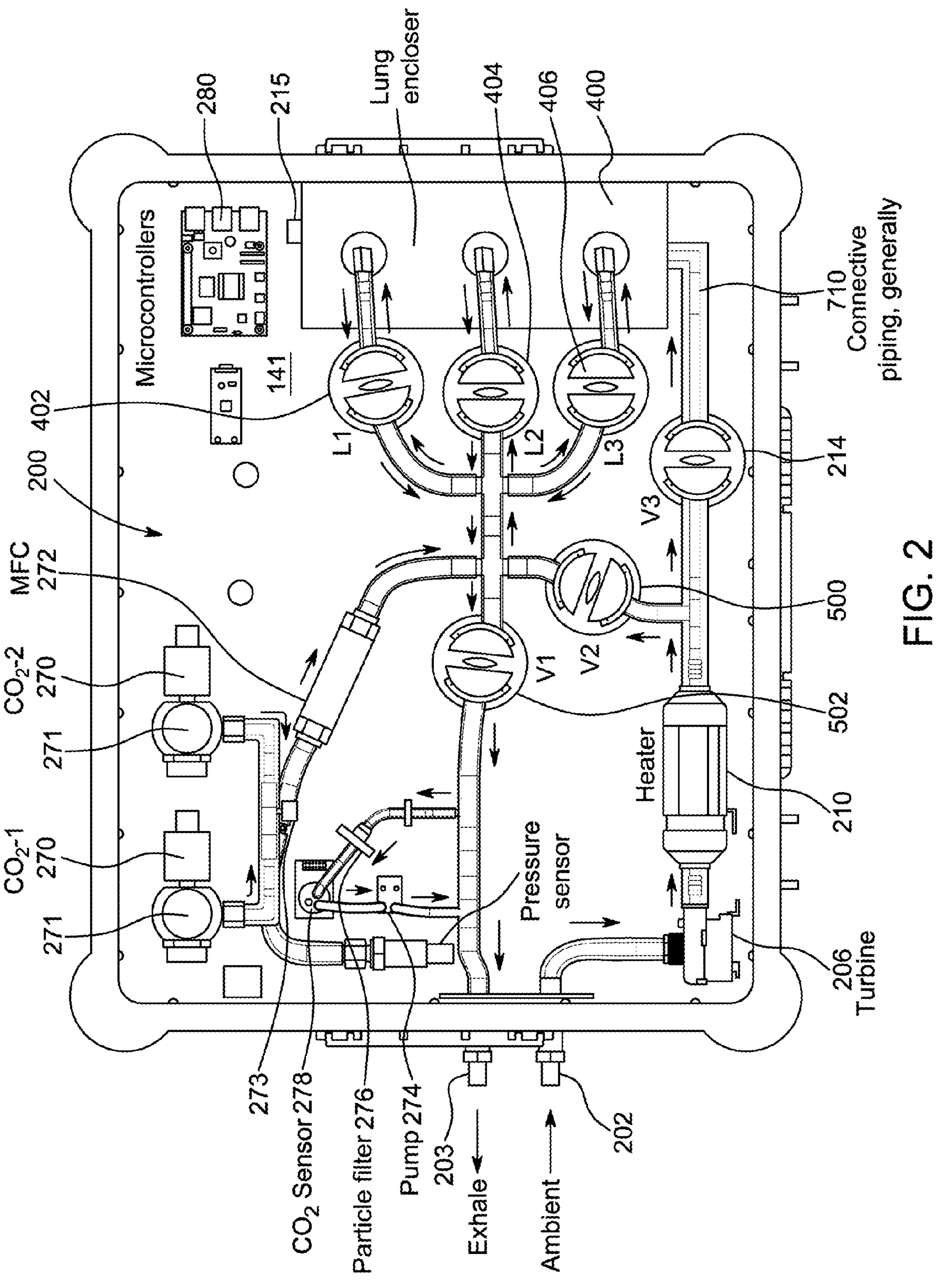
FIG. 2 shows the operational cavity that includes the breathing apparatus components that drive the simulated breathing.
Figure 3:
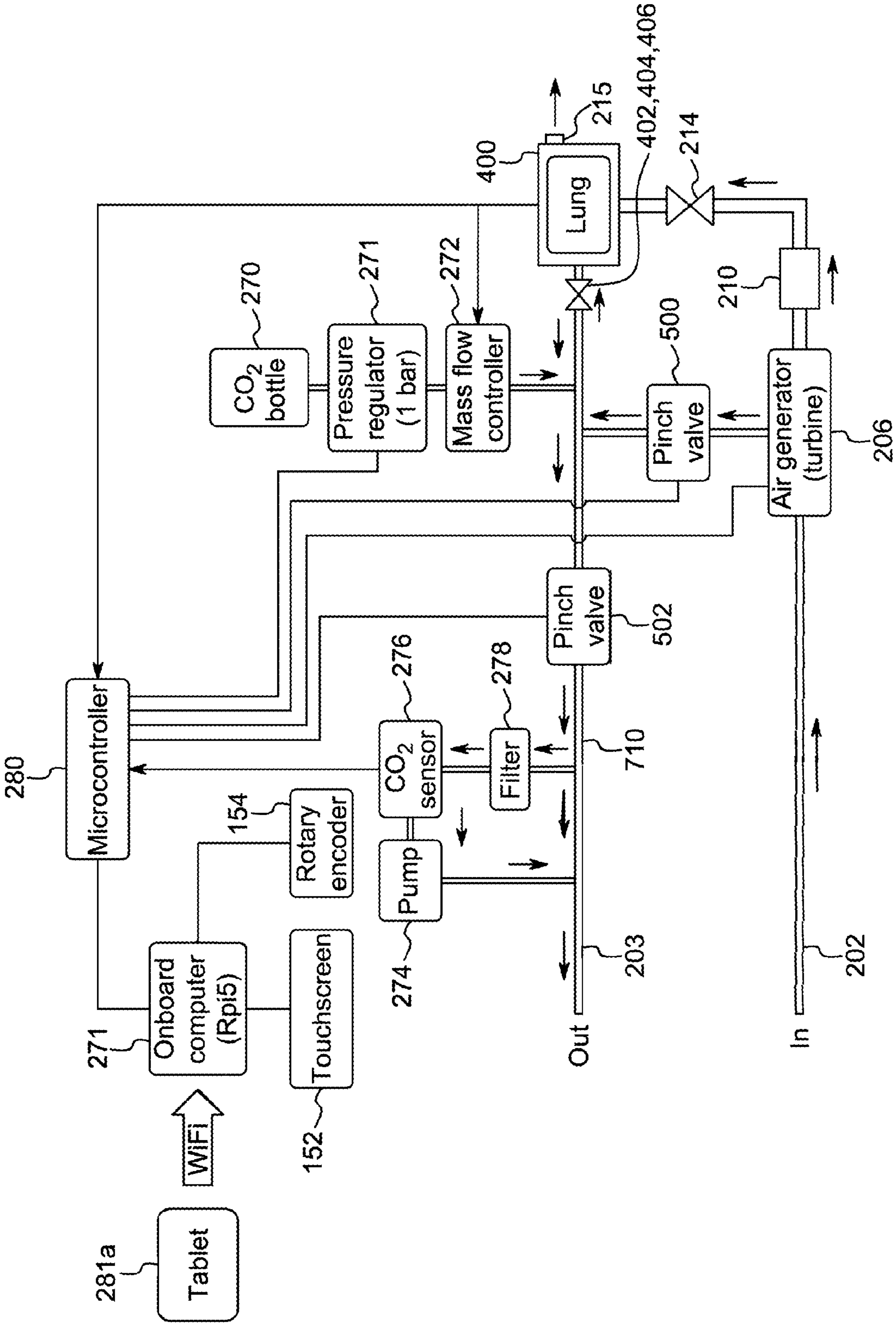
FIG. 3 shows a block diagram of components in the operational cavity.

FIG. 2 shows the operational cavity 200 that includes the breathing apparatus 100 components that drive the simulated breathing. FIG. 3 shows a block diagram of components in the operational cavity 200.

Tracing the flow of ambient air into the breathing apparatus 100, air enters the apparatus through an input trachea connection 202, drawn in through the turbine (pump or fan) 206. The turbine drives the air through the heater 210 that warms the air to approximately body temperature to simulate the human breathing process where the body naturally warms the air when breathing.

Figure 4A:
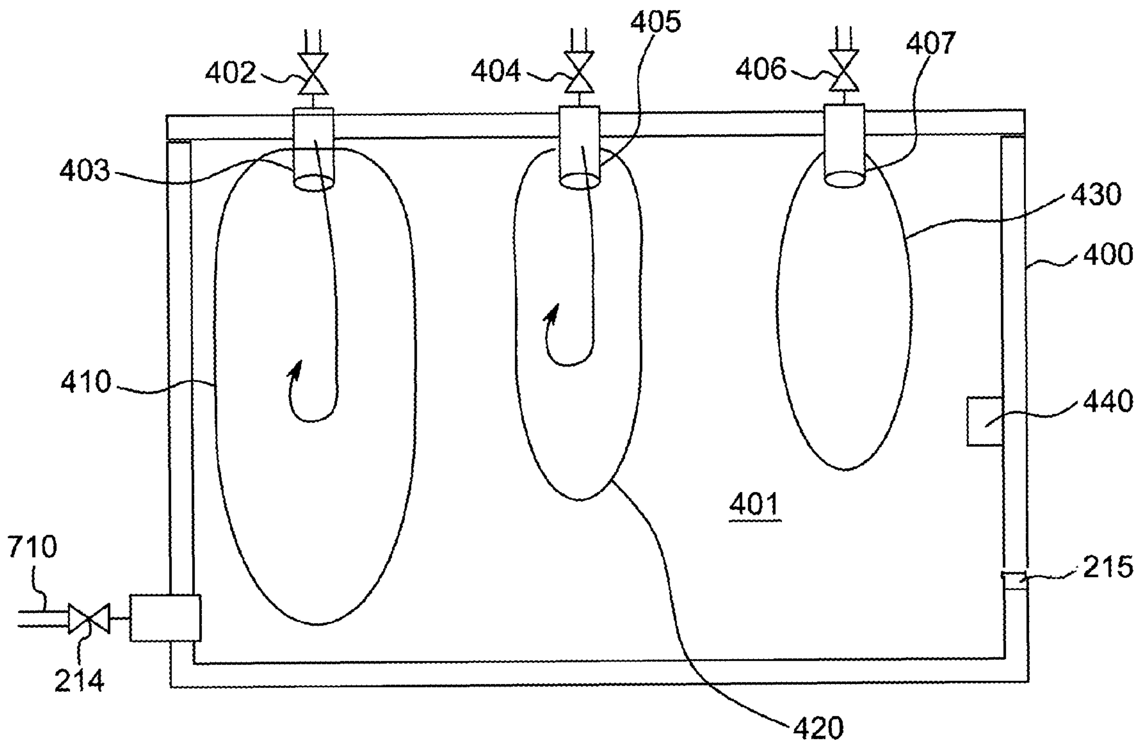
FIGS. 4A and 4B show two embodiments of the lung enclosure.
Figure 4B:
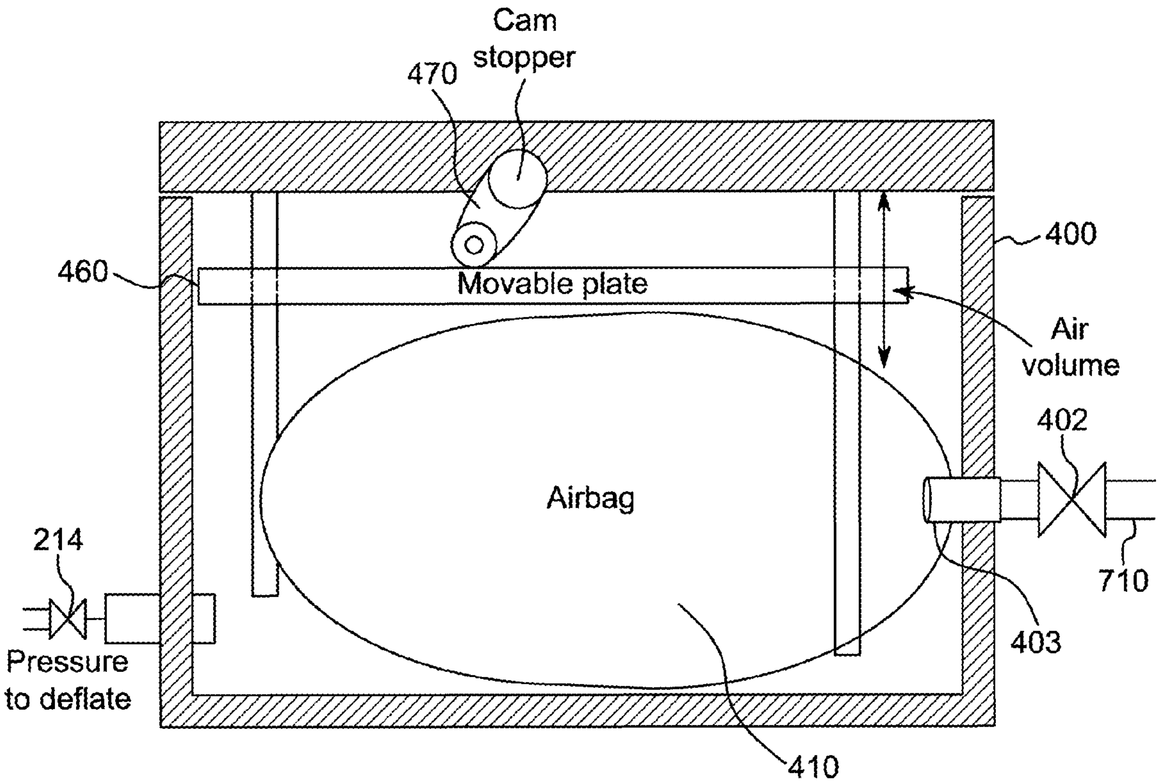

From the heater 210, the now-heated air passes through a positive pressure valve 214 to enter the lung enclosure 400, shown in more detail in FIGS. 4A and 4B. The purpose of the air traveling through the positive pressure valve 214 is to create a positive pressure inside the lung enclosure 400, and the purpose of that positive pressure will be discussed in detail below, but this positive pressure exerts a force on the elastomeric lung bag(s) to simulate an exhale. The lung enclosure 400 may include a pressure sensor to record the positive pressure exerted therein and adjust the positive pressure valve 214 or a lung enclosure relief valve 215 accordingly, to regulate the positive pressure to a level that helps simulate the exhale. The lung enclosure relief valve 215 may vent into the operational cavity 200, or to reduce contamination, be connected directly to atmosphere through the sidewall 143 for venting.

As air leaves the heater 210, it may also be directed through an inhale valve 500, which may be a pinch valve. The inhale pinch valve 500 and an exhale valve 502 (which may also be a pinch valve) operate in detail as described with reference to FIG. 5. When the inhale pinch valve 500 is open, during a simulated inhale, the exhale pinch valve 502 is closed (and vice versa during a simulated exhale). Thus, during the simulated inhale, the heated air passes through the open inhale pinch valve 500, mixes with CO2 from CO2 sources 270 and into the lung enclosure 400, after passing through one or more of the in-parallel lung enclosure valves 402, 404, 406.

Each of the lung enclosure valves 402, 404, and 406 may be open or closed, in any combination, depending on the lung capacity being simulated, as described when discussing FIGS. 4A and 4B, though FIG. 2 shows the lung enclosure embodiment from FIG. 4A, whereas when using the embodiment in FIG. 4B, one or no lung enclosure valve would be required. For this overview discussion of the breathing apparatus 100, however, what happens is that the air passes through at least one open lung enclosure valve 402,404, and/or 406 and into the lung enclosure 400. Inside the lung enclosure 400, one or more of the elastomeric lungs 410, 420, 430 inflates.

As mentioned, CO2 source 270 injects CO2 into the inhale/exhale air stream through a mass flow controller 272 that regulates the flow of CO2 there through. The CO2 could be supplied through any source, but given the size of the breathing apparatus, the amount of CO2 in typical portable 16 cartridges can last several hours. And as shown, 2 such cartridges may be used, though more could also be used. In practice, only one cartridge would typically provide CO2 at a time, while the other(s) could be replaced if they ran out. CO2 flow monitoring at the C02 sensor would trigger an alarm for a user to replace the cartridge and automatically switch CO2 valves 271 open and closed to maintain the flow of CO2 if one source 270 runs out.

A CO2 monitoring system including a CO2 pump 274, CO2 sensor 276, and CO2 filter 278 samples "exhaled" air and based on the sample, controls the mass flow controller 272, and thus the flow of CO2 into an inhale. During an exhale cycle (to be explained shortly), the CO2 pump draws a small sample of exhaled air, what the inventors call a "sip" of such exhaled air, through the CO2 particle filter 204, into the CO2 sensor that detects CO2, and back into the exhaled air stream to preserve the CO2 in the exhale airstream. The C02 particle filter is important because the C02 particle filter 204 may be sensitive to contamination. The CO2 sensor 276 provides C02 measurements to the microcontroller 280 (controlled by and connected to a computer 281), which, based on a desired CO2 level, controls the mass flow controller 272 to regulate the flow of CO2 into the inhaled air stream, as appropriate. The flow of CO2 into the inhale/exhale airstream is at a high enough pressure from a controlled pressure regulator 273, to overcome the inhale and exhale air stream pressure and deliver C02 into this airstream.

The desired CO2 level would reflect the amount of CO2 that would be expected in a human being who had the simulated lung capacity being simulated by the elastomeric lungs 410, 420, 430.

Although it's not shown, similar systems could inject moisture or other compounds into the exhale fluid stream to simulate breathing. For example, if the breathing apparatus goal was to simulate breathing in a carbon monoxide test in which a car interior was subjected to its exhaust, the system could inject appropriate compounds that might be detected in such an instance.

Returning to the inhale/exhale cycle, at a predetermined inhale interval that is based on the simulated lung capacity, the inhale pinch valve 500 closes and the exhale pinch valve 502 and positive pressure valve 214 open. When this happens, the simulated inhale cycle interval has ended, and the simulated exhale cycle interval begins. The positive pressure created by opening the positive pressure valve 214 inside the lung enclosure 400 exerts pressure against the one or more elastomeric lung(s) 410, 420, 430, releasing the air therein back through the lung enclosure valve(s) 402, 404, 406 and through the open exhale pinch valve 502, past the C02 monitoring system components and out the trachea output 203.

After the simulated exhale cycle interval ends, again based on the simulated lung capacity being simulated by the elastomeric lungs 410, 420, 430, the exhale pinch valve 502 and pressure valve 214 close and the inhale pinch valve 500 opens, starting another inhale cycle. Also, as the inhale cycle begins and once the positive pressure valve 214 closes, the positive pressure inside the lung enclosure 400 vents through the pressure relief valve 215, releasing the positive pressure therein.

Figure 6:
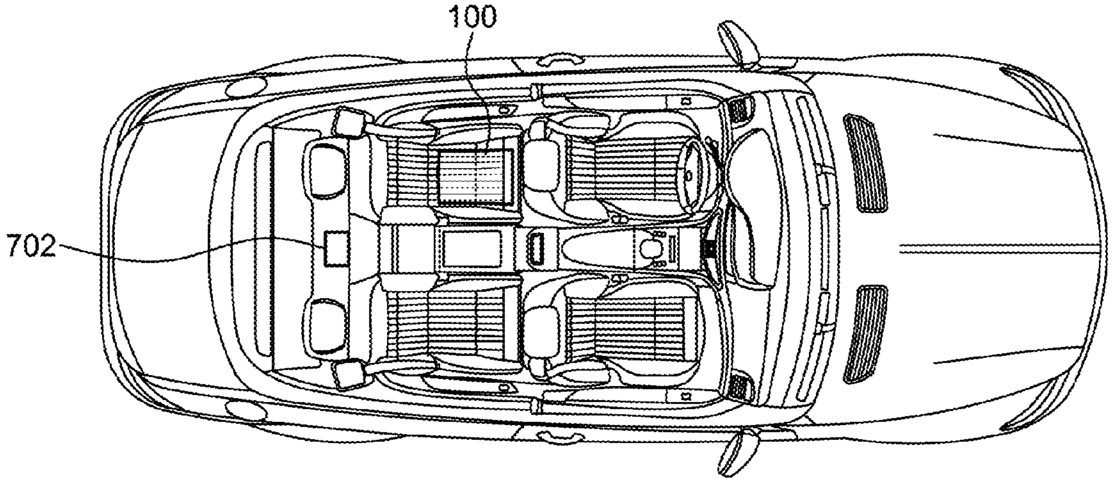
FIG. 6 shows an automobile with a CO2 detection system in use with the breathing apparatus.

The simulated exhale that exits the breathing apparatus (100) contains a similar content of compounds as breathed air. This simulated breathed air may be monitored by a CO2 detection system 702 in, for example, an automobile as shown in FIG. 6. In testing of CO2 detection systems 702 and automobile configurations, the breathing apparatus closely simulates the breathing cycles of a human, which can lead to the development of better CO2 detection systems, or rating the ability of CO2 detection systems to detect dangerous conditions in a car.

The microcontroller 280, with settings pre-determined through the computer 281 or other wireless device 281*a*, can control all of the breathing apparatus's controllable components, including valves, flow controllers and regulators, pumps, heaters, turbines, sensors, and detectors.

FIG. 4A shows a first embodiment of the lung enclosure 400, with the lung enclosure valves 402, 404, 406 shown and the pressure relief valve 215, all previously discussed. FIG. 4A also shows the lung enclosure interior 401, which is under positive pressure (measured by pressure sensor 440 and fed back to the microprocessor 280 for monitoring) from pressurized air delivered by the turbine 206. In this embodiment, three elastomeric lungs 410, 420, and 430, perhaps of different volumetric capacities, inflate during the inhale cycle, depending on which of the three lung enclosure valves 402, 404, 406 are open as determined according to the simulated lung capacity desired.

When the breathing apparatus 100 begins its exhale cycle, the positive pressure therein exerts pressure on the elastomeric lungs 410, 420, 430 driving the air therein out as previously described.

The elastomeric lungs 410, 420, 430 may be sealed around lung enclosure ports 403, 405, 407 respectively in such a way that they do not allow inhale or exhale cycle fluid to escape into the lung enclosure interior 401, but additionally in a way in which the elastomeric lungs 410, 420, 430 may be easily replaced when necessary. Thus, as shown, the elastomeric lungs 410, 420, 430 include a port opening 412, 422, 432 that overlaps the lung enclosure port, and these port components may be clamped, sealed, glued, or otherwise removably joined to one another.

FIG. 4B shows an alternate embodiment of the lung enclosure 400. In this embodiment, there is a single elastomeric lung 410 of a larger capacity within the lung enclosure interior 401, with other similarly numbered components being the same as in FIG. 4A. To adjust lung capacity in this embodiment, there need only be a single lung enclosure valve 402 (instead of three). Adjusting the capacity can be done by directing a lung enclosure plate 460 downwards (as oriented) along rails 462 to decrease the simulated lung capacity, or upwards, to increase it, through any adequate means, including rotating the cam mechanism 470 connected to the plate 460.

Figure 5:
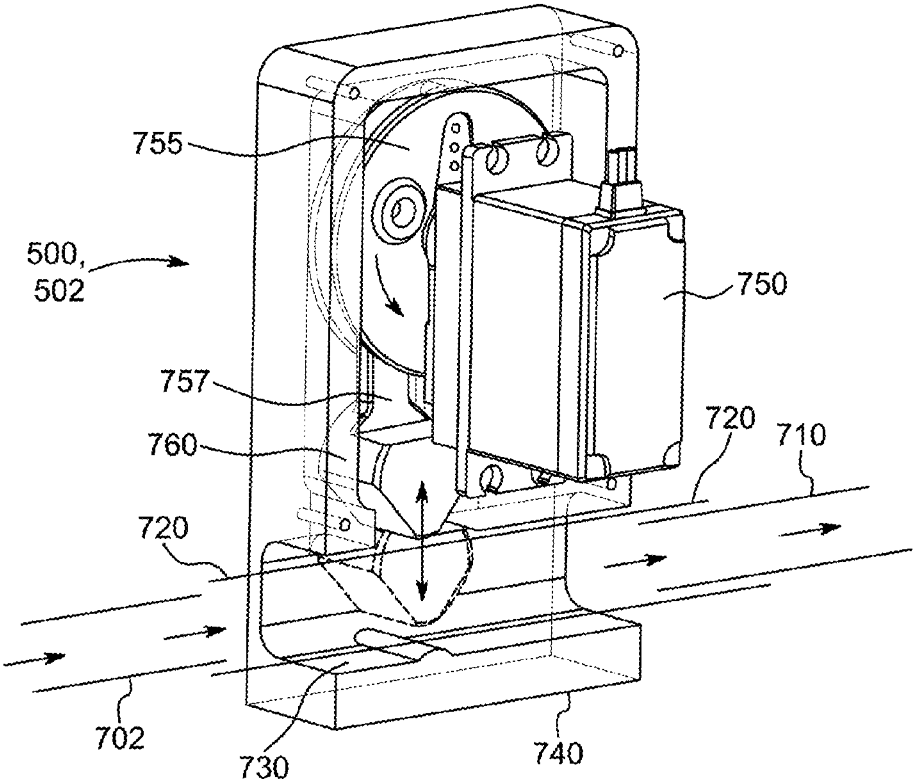
FIG. 5 shows the pinch valve.

FIG. 5 shows a graphical representation of one of the inhale/exhale pinch valves 500, 502. Although the air piping shown and described would be expected to be sturdy and not subject to pinch closures, such piping 710 connects at the pinch valves 500, 502 to a more flexible tubing 720 in a sealed arrangement. The flexible tubing 720 extends through a channel 730 inside the body 740 of the pinch valve. At the respective inhale/exhale cycle, the microcontroller 280 operates the motor 750, which turns the rotor 755, which drives the piston 757, having the softly pointed head 760 downwards (shown in phantom) and into the flexible tubing 720 in the channel 730, restricting air flow. A second signal at the end of the respective inhale-exhale cycle turns to rotor 755, withdrawing the piston 757 and head 760, opening the flexible tubing 720. Each open and closing of the flexible tubing 720 is the respective pinch valve 500, 502 opening or closing as previously described.

The two main features that make pinch valves attractive are first, as pinch valves, they open and close flow through a tube 720 by squeezing the soft silicone tube 720, thereby restricting flow. While this does not necessarily guarantee a perfect restriction of all flow through the valves 500, 502 that could be achieved, even with a modest amount of back flow through the valve allows the breathing apparatus 100 will perform its function. The second advantage of the pinch valve is that the valve itself is not contaminated with the fluid that is inside the tube because the tube's content is simply ambient air. There are some benefits in terms of moisture retention that we think is a small advantage for using pinch valves. Furthermore, pinch can be relied upon to prevent leakage into the lung interior enclosure 401, and thus into the vehicle leading to problems with measurement and testing of the CO2 sensing system in the car. The operating pressure of pinch valves is between 0 and 7 psi, which is in the range for physiologic breathing. These pinch valves 500, 502 may also be of a latching design, which means there is a mechanism inside the valve that holds the valve closed without solenoid energy, thus making for efficient use of electrical power.

As described, air may enter the turbine through an inlet drawing gas from the inlet trachea connection 202 that may be attached to a crash test dummy or other human surrogate.

In operation, the breathing apparatus 100 may be placed within cabin of the vehicle or enclosure to be tested (such as an automobile in FIG. 6). The apparatus 100 is turned on and the user uses their wireless device 281*a* or the screen 152 to set the breathing parameters including the respirator rate, CO2 concentration, and tidal volume. Power for the apparatus can be provided by an external off-the-shelf battery, such as the 240 Wh Backup lithium battery, standard domestic household power, or another power source compatible with the device. The device input and output trachea connections 202, 203 are placed anywhere in the vehicle cabin, typically near the head of a would-be occupant. Alternatively, the connections could be attached to tubes and routed through the nostrils and mouth of an anthropomorphic test device (crash test dummy) or other mannequin simulating a human or animal. In this configuration, the breathing device could be used to drive chest rise and fall in the mannequin, which is important for occupant sensing systems that detect the motion of the body due to breathing, either in combination with or without a CO2 sensing system. These alternative sensing systems may include camera, lidar, or radar sensors that detect the motion of the chest during normal respiration. Such sensors could be used by themselves, or with CO2 sensors to create a more robust, multi-technology occupant sensing system.

With the breathing apparatus 100 simulating a breathing human or animal, a forgotten occupant event is simulated by opening the doors and closing them shortly thereafter. Through the wireless interface, the device can be controlled as if the user was at the main interface but without disturbing the quiescent nature of the cabin with closed doors. When the test is over, the apparatus 100 may be turned off and removed from the vehicle. Subsequently, the CO2 reservoirs are replenished as needed and the battery charged, if required, to make the apparatus ready for the next use.

In alternate embodiments, solenoid-actuated valves are a possible alternative for the pinch valve, wherein one or more electronic coils move the valve mechanism to control the flow. In addition, motorized ball valves are an alternative to the pinch valves. In the motorized ball valve, one or more electric or pneumatic motors turn a mechanical ball valve to regulate flow.

An alternative to the turbine is a centrifugal blower, where a wheel of rotating angled blades pulls air in at its center and exhausts it at its periphery. Additionally, an axial fan, including a series of fans, could drive the air. A piston-cylinder device could also pump air, which would obviate the need for valves.

The valves described herein may be configured to be adjustable between open and closed states, and/or restrict and control flow between the open and closed states.

The inhale and exhale cycles may be determined based on the simulated lung capacity (a child may have a higher respiratory rate than an adult) or other factors. These cycles may also self-adjust to be shorter or longer during a test simulation, such that as CO2 or other conditions like heat or cold take place inside a test vehicle, for example, the cycles may speed up or slow down, as appropriate. These cycle times and changes can be programmed in advance or modified in the test manually.

The terms air and fluid used herein may be interchanged.

While the invention has been described with reference to the embodiments above, a person of ordinary skill in the art would understand that various changes or modifications may be made thereto without departing from the scope of the claims.

We claim:

1. A breathing simulation apparatus comprising:

a trachea input;

a positive pressure valve in fluid communication with the trachea input;

a lung enclosure in fluid communication with the positive pressure valve, wherein the lung enclosure is sealed such that fluid flow through the trachea input and through the positive pressure valve creates a positive pressure inside the lung enclosure, where in the lung enclosure includes at least one simulated lung therein, wherein the simulated lung is not in fluid communication with fluid creating the positive pressure inside the lung enclosure;

an exhale valve in fluid communication with the lung enclosure and a trachea output;

an inhale valve in fluid communication with the positive pressure valve and the lung enclosure;

wherein during a simulated inhale cycle, the positive pressure valve and exhale valve are closed, the inhale valve is open, and fluid flows from the trachea input through the inhale valve and into the at least one simulated lung; and wherein during a simulated exhale cycle, the positive pressure valve and exhale valve are open, the inhale valve is closed, fluid flows from the trachea input through the positive pressure valve and into the lung enclosure creating positive pressure therein on the at least one simulated lung); and due to this positive pressure, the at least one simulated lung releases fluid therein though the lung enclosure, then through the exhale valve, and then though the trachea output.

2. The breathing simulation apparatus of claim 1, further comprising a turbine, pump, or fan that draws fluid in through the trachea input and during an exhale cycle, drives the fluid though the open positive pressure valve and into the lung enclosure to create the positive pressure.

3. The breathing simulation apparatus of claim 1, wherein during an inhale cycle, the turbine, pump, or fan drives fluid through the inhale valve and into the at least one simulated lung.

4. The breathing simulation apparatus of claim 1, wherein the simulated inhale cycle and the simulated exhale cycle are defined by a predetermined and adjustable time interval.

5. The breathing simulation apparatus of claim 1, wherein the inhale valve and exhale valve are pinch valves.

6. The breathing simulation apparatus of claim 5, wherein the inhale and exhale pinch valves each include a flexible tube therethrough, and a piston pinches the flexible tube to close the inhale and exhale pinch valves.

7. The breathing simulation apparatus of claim 1, wherein the at least one simulated lung is an elastomeric bag.

8. The breathing simulation apparatus of claim 1, wherein the lung enclosure includes more than one at least one simulated lung, and for each of the more than one at least one simulated lungs, there is a lung enclosure valve between the inhale valve and each of the more than one at least one simulated lungs, wherein opening and closing the lung enclosure valves increases or decreases a simulated lung capacity in the breathing apparatus.

9. The breathing simulation apparatus of claim 1, wherein there is at least one simulated lung, and to increase or decrease a simulated lung capacity in the breathing apparatus, one or two plates inside the lung enclosure presses against or moves away from the one at least one simulated lung to increase or decrease the simulated lung capacity.

10. The breathing simulation apparatus of claim 1, further comprising a heater that warms the fluid.

11. The breathing simulation apparatus of claim 1, further comprising a carbon dioxide source that injects carbon dioxide into the fluid passing between the lung enclosure and the exhale valve to simulate carbon dioxide emitted during breathing.

12. The breathing simulation apparatus of claim 11, wherein a pressure regulator and mass flow controller act together to control the volume of carbon dioxide injected.

13. The breathing simulation apparatus of claim 1, wherein a microcontroller operable by a computer or wireless device controls the inhale valve, exhale valve, and positive pressure valve.

14. The breathing simulation apparatus of claim 1, contained within a case that can be opened and closed.

15. A method of detecting carbon dioxide buildup in a vehicle comprising:

providing a carbon dioxide detector in the vehicle;

providing a breathing simulation apparatus comprising:

a trachea input;

a positive pressure valve in fluid communication with the trachea input;

a lung enclosure in fluid communication with the positive pressure valve, wherein the lung enclosure is sealed such that fluid flow through the trachea input and through the positive pressure valve creates a positive pressure inside the lung enclosure, where in the lung enclosure includes at least one simulated lung therein, wherein the simulated lung is not in fluid communication with fluid creating the positive pressure inside the lung enclosure;

an exhale valve in fluid communication with the lung enclosure and a trachea output;

an inhale valve in fluid communication with the positive pressure valve and the lung enclosure;

wherein during a simulated inhale cycle, the positive pressure valve and exhale valve are closed, the inhale valve is open, and fluid flows from the trachea input through the inhale valve and into the at least one simulated lung; and wherein during a simulated exhale cycle, the positive pressure valve and exhale valve are open, the inhale valve is closed, fluid flows from the trachea input through the positive pressure valve and into the lung enclosure creating positive pressure therein on the at least one simulated lung; and due to this positive pressure, the at least one simulated lung releases fluid therein though the lung enclosure, then through the exhale valve, and then though the trachea output;

operating the breathing apparatus to simulate inhale and exhale cycles;

closing the doors of the vehicle; and measuring and recording the carbon dioxide buildup in the vehicle using the carbon dioxide detector.

* * * * *